United States Patent [19]

Krimmer et al.

[11] Patent Number: 4,918,224

[45] Date of Patent: Apr. 17, 1990

[54] METHOD OF PREPARING SALTS OF N-ACETYL CYSTEINE OR N-ACETYL HOMOCYSTEINE

[75] Inventors: Hans-Peter Krimmer, Frankfurt; Karlheinz Drauz, Freigericht, both of Fed. Rep. of Germany

[73] Assignee: Degussa Akteingesellschaft, Frankfurt am Main, Fed. Rep. of Germany

[21] Appl. No.: 230,026

[22] Filed: Aug. 9, 1988

[30] Foreign Application Priority Data

Aug. 21, 1987 [DE] Fed. Rep. of Germany ....... 3727896

[51] Int. Cl.$^4$ ................ C07C 149/243; C07C 149/247
[52] U.S. Cl. .................................... 562/557; 562/556
[58] Field of Search ................................ 562/556, 557

[56] References Cited

PUBLICATIONS

Krimmer, Chem.-Ztg., 111 pp. 357–361 (1987).

Primary Examiner—Michael L. Shippen
Attorney, Agent, or Firm—Cushman, Darby & Cushman

[57] ABSTRACT

Salts of N-acetyl cysteine and N-acetyl homocysteine are prepared by reacting acetonitrile with cysteine or homocysteine in an aqueous or aqueous-organic medium adjusted to a pH in the range of 8 to 10 with a base supplying the cation of the salt. The reaction is carried out at a temperature in the range of 0° C. to the boiling temperature of the reaction mixture.

5 Claims, No Drawings

METHOD OF PREPARING SALTS OF N-ACETYL CYSTEINE OR N-ACETYL HOMOCYSTEINE

The invention relates to a method of preparing salts of the general formula:

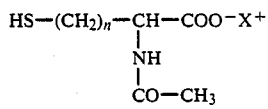

in which n signifies the number 1 or 2 and $X^+$ an alkali metal ion, an equivalent of an alkaline earth metal ion, an ammonium ion or a protonium salt of an organic base.

BACKGROUND OF THE INVENTION

Salts of N-acetyl cysteine and N-acetyl homocysteine are known. They are of interest as intermediates for peptide synthesis, as active pharmaceutical substances or in cosmetic preparations. For example, the sodium salt and the ammonium salt of N-acetyl-L-cysteine are used as a mucolytic agent.

The preparation of salts of N-acetyl cysteine and N-acetyl homocysteine encounters difficulties in so far as the selective N-acetylation of mercapto-α-amino acids is only possible with considerable effort.

SUMMARY OF THE INVENTION

In accordance with the present invention, salts of N-acetyl cysteine and of N-acetyl homocysteine can be directly prepared in a quite simple manner.

In accordance with the present invention, acetonitrile is reacted with cysteine or homocysteine in an aqueous or aqueous-organic medium adjusted to a pH in the range of 8 to 10 by a base supplying the $X^+$ cation. The reaction is carried out at a temperature in the range of 0° C. to the boiling temperature of the reaction mixture. After the reaction is over, the solvent is evaporated under reduced pressure.

It is advantageous to add the acetonitrile in a threefold to fivefold molar excess since this can shorten the reaction time required. A slight molar excess of approximately 10 to 20% is also recommended for the base used.

The reaction between the acetonitrile and the mercapto-α-amino acid is preferably performed is such a manner that the reaction mixture is heated under reflux to a boil. It then generally requires a reaction time between 2 and 8 hours.

It is advantageous to perform the reaction under an inert gas (e.g. nitrogen) atmosphere in order to minimize the danger of an oxidation of the mercapto compounds to the corresponding disulfides. It is especially advantageous to pass the inert gas through the reaction mixture during the entire reaction in order to simultaneously expel the ammonia which is produced, which can shorten the required reaction time.

The following can be considered as potential bases for supplying the $X^+$ cation: Alkali metal hydroxides or alkaline earth metal hydroxides such as lithium hydroxide, sodium hydroxide, potassium hydroxide, magnesium hydroxide or calcium hydroxide; alkali metal carbonates or alkaline earth metal carbonates or hydrogen carbonates such as lithium carbonate, sodium carbonate, potassium carbonate, magnesium carbonate or calcium carbonate or hydrogen carbonate; ammonia; alkyl amines, dialkyl amines or trialkyl amines, such as methyl, ethyl, propyl, isopropyl, n-butyl, isobutyl, sec-butyl, tert-butyl, dimethyl, diethyl, di-n-propyl, diisopropyl, di-n-butyl, diisobutyl, di-sec-butyl, trimethyl, triethyl, tri-n-propyl, diisopropylmethyl or diisopropylethyl amine; or unsaturated heterocyclic bases such as pyridine, α-, β-or τ-picoline, lutidine, quinoline, isoquinoline, collidine, pyrollidine, piperidine, piperazine, N-methylpiperidine or quinuclidine.

If inorganic bases or readily water-soluble organic bases are added, pure water is suitable as the reaction medium. If organic bases are used, which are less water-soluble, the use of an aqueous-organic reaction medium is recommended, that is, a mixture of water and an organic solvent which is at least partially miscible with water. Suitable solvents are e.g. aliphatic alcohols with 1 to 4 carbon atoms and ethers such as tetrahydrofuran or 1,4-dioxane.

The method of the present invention can be carried out e.g. in such a manner that all starting materials are dissolved in water or in a suitable aqueous-organic medium and the reaction mixture is heated under reflux to a boil until no unreacted mercapto-o-amino acid can be observed in a specimen obtained by high-pressure liquid chromatography. Then the solvent is evaporated under reduced pressure until the desired salt begins to crystallize out. After the mixture has been cooled, the precipitated crystals are separated and dried.

If no crystallization occurs during the evaporation of the solvent, it can be brought about by cooling the residue and digesting it with a suitable solvent, e.g. ethanol.

The method of the invention has the advantage, when reacting optically active cysteine, no racemization takes place.

The invention is explained in more detail in the following examples:

EXAMPLE 1

12.3 g (0.3 mole) acetonitrile were heated in 250 ml water for one hour to a boil under a nitrogen atmosphere. Then the mixture was cooled to 60° C. and 12.1 g (0.1 mole) L-cysteine and 8.7 g (0.126 mole) 25% by weight aqueous ammonia were added. The reaction mixture was heated to a boil and refluxed for 5 hours while gently passing nitrogen through it. Then all volatile components of the reaction mixture were evaporated under reduced pressure. The residue was digested with 10 ml ethanol and the resulting crystals were separated by suction and dried. 15.8 g (87% of theory) colorless ammonium salt of N-acetyl-L-cysteine were obtained with a melting point of 148°–149° C. (decomposition).

$[\alpha]^{25}_D = 20.3°$ (c=5; $H_2O$)

$^1$H-NMR (DMSO-$d^6$): $\tau=1.87$ (s; 3H, acetyl-$CH_3$), 2.76 (mc; 2H, β-$CH_2$), 4.02 (m; 1H, α-H), 6.34 (wide; 5H, $NH_4^+$ and SH), 7.50 (d; 1H, NH).

EXAMPLE 2

20.5 g (0.5 mole) acetonitrile, 12.1 g (0.1 mole) L-cysteine and 6.9 g (0.05 mole) potassium carbonate were heated under nitrogen in 250 ml water to a boil and refluxed for 4 hours. Then, carbon dioxide gas was passed through the reaction mixture and it was heated 30 minutes longer. The reaction mixture was concentrated by evaporation under reduced pressure until the crystallization began. After the mixture had cooled off, the precipitated crystals were separated by suction and dried. 18.2 g (91% of theory) colorless potassium salt of N-acetyl-L-cysteine were obtained.

Example 3

20.5 g (0.5 mole) acetonitrile, 12.1 g (0.1 mole) L-cysteine and 4.4 g (0.11 mole) sodium hydroxide were heated under nitrogen in 250 ml water to a boil and refluxed. The course of the reaction was followed with high-pressure liquid chromatography. After the reaction was completed, the process was continued as in Example 2. 14.6 g (80% of theory) colorless sodium salt of N-acetyl-L-cysteine were obtained.

What is claimed is:

1. A method of preparing salts of the general formula

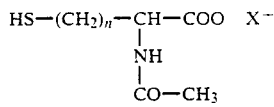

in which n signifies the number 1 or 2 and $X^+$ is an alkali metal ion, an equivalent of an alkaline earth metal ion, an ammonium ion or a protonium salt of an organic base, said method comprising reacting acetonitrile with cysteine or homocysteine in an aqueous or aqueous-organic medium adjusted to a pH in the range of 8 to 10 by a base supplying the $X^+$ cation, at a temperature in the range of 0° C. to the boiling temperature of the reaction mixture and, after the reaction is over, removing the solvent.

2. A method as set forth in claim 1 in which the solvent is removed by evaporation under reduced pressure.

3. A method as set forth in claim 1 in which the reaction is performed under an inert gas atmosphere.

4. A method as set forth in claim 3 in which the inert gas is nitrogen.

5. A method as set forth in claim 4 in which the nitrogen is passed through the reaction mixture during the reaction.

* * * * *